United States Patent [19]
Hockele et al.

[11] 3,987,099
[45] Oct. 19, 1976

[54] PROCESS FOR HYDROGENATION OF DODECANEDIOIC ACID DINITRILE

[75] Inventors: Gunter Hockele, Marl; Gerhard Ludwig, Lippramsdorf, both of Germany

[73] Assignee: Chemische Werke Huls Aktiengesellschaft, Marl, Germany

[22] Filed: Oct. 22, 1974

[21] Appl. No.: 517,023

Related U.S. Application Data

[63] Continuation-in-part of Ser. No. 139,241, April 30, 1971, abandoned.

[30] Foreign Application Priority Data

May 2, 1970 Germany............................ 2021522

[52] U.S. Cl. ........................ 260/584 R; 260/583 K; 252/458; 252/474
[51] Int. Cl.² ........................................ C07C 120/08
[58] Field of Search.......... 260/583 P, 583 K, 584 R

[56] References Cited
UNITED STATES PATENTS 2,287,219   6/1942   Young et al. .................... 260/583 K
2,652,430   9/1953   Finch et al. ...................... 260/583 P
3,558,709   1/1971   Hockele ........................... 260/584 R

*Primary Examiner*—Allen B. Curtis
*Attorney, Agent, or Firm*—Millen, Raptes & White

[57] ABSTRACT

A process for the catalytic hydrogenation of dodecanedioic acid dinitrile to the corresponding primary amine employing a hydrogenation catalyst which comprises 5-35% by weight of at least one of catalytically active cobalt and nickel as the active component supported on one or more oxides of aluminum, silicon, titanium and iron, wherein the specific surface area of the support material is $0.01-1.2 m^2/g.$, the pore volume is 0.05–0.4 ml./g., the annealing loss is less than 0.1% and the extractable alkalinity of the support is 0.08–20% by weight of the support. Sufficient alkali is present in the hydrogenation diluent to ensure that the desired alkali concentration remains on the catalyst surface, thereby extending the useful life of the catalyst.

6 Claims, No Drawings

PROCESS FOR HYDROGENATION OF DODECANEDIOIC ACID DINITRILE

CROSS REFERENCE TO RELATED APPLICATION

This is a Continuation - in - Part of copending, commonly assigned U.S. patent application Ser. No. 139,241 filed Apr. 30, 1971 and now abandoned.

BACKGROUND OF THE INVENTION

This invention relates to a process for the hydrogenation of nitriles and dinitriles to the corresponding primary amines in the presence of a supported cobalt and/or nickel catalyst, wherein the support is an oxide of aluminum, silicon, titanium, iron, or a mixture thereof.

The catalytic hydrogenation of nitriles and dinitriles in the presence of ammonia is perferably carried out with the use of solid-bed catalysts obtained by the precipitation, on porous supports, or thermally decomposable cobalt salts and/or nickel salts in combination with other metallic salts which decompose on heating to difficultly reducible oxides, e.g., salts of chromium and manganese. Silica gel, silicic acid, aluminum silicates, pumice and aluminum oxides have been suggested as suitable supports for these catalysts (German Pat. No. 964,864). Using such supported catalysts, the hydrogenation of nitriles and dinitriles usually can be conducted at about 100° C. under a pressure of 150–300 atmospheres in the presence of ammonia and hydrogen. Optionally, the reaction can be conducted in an inert solvent in order to obtain advantageous removal of the heat of reaction.

These conventional catalysts have an inadequate hydrogenation lifetime. Especially when employed in the presence of diluents, the catalyst bed is clogged up, within a relatively short reaction time, so that the catalyst must be replaced.

It is an object of this invention to provide a hydrogenation process employing supported hydrogenation catalysts which have a longer lifetime. Other objects will be apparent to those skilled in the art to which this invention pertains.

SUMMARY OF THE INVENTION

Briefly, the above and other objects are attained in one aspect of this invention by providing a process for the catalytic hydrogenation of dodecanedioic acid dinitrile to the corresponding primary amine, which comprises:

hydrogenating dodecanedioic acid dinitrile with a hydrogenation catalyst comprising 5 – 35% by weight of at least one of catalytically active cobalt and nickel as the active component supported on one or more of aluminum oxide, silicic acid or silica containing small amounts of the oxides of Na, Fe, Ca and Mg wherein the specific surface area of the support material is 0.1 – 0.8 m$^2$/g., the pore volume thereof is 0.2 – 0.4 ml./g., the annealing loss is less than 0.1% and the extractable alkalinity of the support is 0.1 – 10% by weight of the support, said hydrogenation being conducted in the presence of a diluent and a sufficient amount of alkali to ensure that said alkali concentration remains on the surface of the hydrogenation catalyst.

DETAILED DISCUSSION

The supports for the catalysts of this invention can be pure oxides, e.g. aluminum oxide, silicic acid, synthetic titanium dioxide, or mixtures thereof. Aluminum oxide and silicic acid are preferred. However, impure oxides, e.g. those containing one or more of sodium, potassium, calcium, magnesium, in the bound form, alone or in a mixture with one another, can also be present.

The support material for the catalysts of this invention has a surface area of 0.01 – 1.2 m$^2$/g., preferably 0.1 – 0.8 m$^2$/g. When aluminum oxide is employed, a surface area of <0.05 to 0.5 m$^2$/g., is preferred. The support material, unless it already possesses the desired specific surface area, is sintered at sufficiently high temperatures until the specific surface area has decreased to below 1.2 m$^2$/g. Most supports require sintering at a temperature of 900° – 1800° C. for about 1 – 10 hours. Specific surface is determined according to the method of S. Brunauer, P.H. Emmett, and E. Teller, "Journal of the American Chemical Society", 60, p. 309 (1938).

Another characterizing feature of the catalysts of this invention is the free alkali content of the support material, which is about 0.08 – 20%, preferably 0.1 – 10%, calculated as the oxide. The term "free alkali content" means the amount of alkali which comes into effective contact with the reactants. The free alkali content of the support material is determined as follows: One part by volume of the support material is twice digested with 2 parts by volume of 10% strength hydrocholoric acid for 2 hours at 20° C. Thereafter, the material is washed free of acid with distilled water and then dried. During the entire procedure, care must be taken that the grain of the support material remains undamaged. The difference in weight between the acid treated support material and the untreated support material is the free alkali content.

To adjust the alkali content of the surface, the hydroxides and carbonates of the alkali metal, preferably those of sodium and potassium, can be employed. The desired alkali content is set in accordance with conventional methods.

The free alkali content of the support material can be increased by the application of, for example, dilute aqueous soda solution, NaOH—, KOH—, or K$_2$CO$_3$— solution; this can be done, for example, by spraying, suitably with simultaneous drying.

Another characterizing feature of the catalysts of this invention is the pore volume of the support material, which is to be 0.05 – 0.4 ml./g., preferably 0.2 – 0.4 ml./g. Pore volume is determined as follows: A sample of the support material is evacuated (aspirator vacuum). A measured amount of water is then poured theron. The support material is drained and the non-absorbed water is measured. The water retained is calculated and the pore volume is expressed as the volume of water retained by the drained support material. Suitably, after the water has been poured over the support, an aspirator vacuum can be applied for control purposes to determine whether any more gas bubbles are formed. Of course, no loss of water may be incurred during this step.

The annealing loss of the support material employed in forming the catalysts of this invention is less than 0.1% by weight. The weight loss of the support material is determined by the following method: A pulverized test sample is heated for several hours, e.g. about 6 hours, at 850° C, then cooled in a dessicator. After weighing it is heated again for some time at 850° C and is weighed once more. If there is no loss in weight, the sample is constant in weight. The difference in weight between the first and the last weighing is the annealing loss.

The proportion of the activating metal, i.e., cobalt and/or nickel, in the total catalyst is generally about 5 – 35% by weight, preferably about 8 – 25% by weight.

In addition to cobalt and/or nickel, other activating metals can be present, individually or in admixture. Suitable additional activating metals include but are not limited to chromium, manganese and silver. Manganese and/or silver are preferred. The activating metals are present in the finished catalyst as oxides or mixed oxides. These additional metals, when present, are generally employed in amounts of 0.05 – 12% by weight, preferably 0.2 – 8% by weight, based on the total catalyst.

The catalysts of this invention are prepared by impregnating the support with an aqueous solution of a soluble salt of the selected activating metal or metals which decomposes on heating to the corresponding oxides, e.g. nitrates, acetates, etc. Preferred are the mixed nitrates of cobalt, manganese and silver. Thereafter, the water is evaporated and the salts are decomposed to the corresponding oxides at an elevated temperature, e.g. about 250° – 400° C. To activate the catalyst, the catalyst is then reduced with hydrogen at an elevated temperature, e.g. about 150° – 350° C.

The catalysts of this invention are particularly suited for the hydrogenation of nitriles to amines. Examples of such nitriles are mono-nitriles, dinitriles and polynitriles, particularly aliphatic nitriles containing from one to fourteen carbon atoms, e.g., of the formula $CH_3(CH_2)_n-C \equiv N$ wherein $n$ is 0 – 12, preferably 4 – 10, especially 8 – 10, e.g., acetonitrile, propionitrile, butyronitrile, etc. Especially preferred are dinitriles, e.g., those of the formula $N \equiv C(CH_2)_n-C \equiv N$ wherein $n$ is 2 – 12, preferably 4 – 10 and especially 8 – 10 e.g., ethylene dinitrile, tetramethylene dinitrile, hexamethylene dinitrile, octamethylene dinitrile, decamethylene dinitrile, etc.

The catalysts employed in the process of this invention exhibit an exceptional freedom from clogging and retention of activity in the hydrogenation of nitriles to amines, even when conducted in the presence of diluents over short reaction times, which conditions readily clog the catalyst bed of similar catalysts employed in the prior art, e.g., those described in Hoeckele U.S. Pat. No. 3,588,709. They are especially advantageous for the hydrogenation of larger chain nitriles, e.g., of 6 – 12 carbon atoms.

The hydrogenation of nitriles or dinitriles is conducted at temperatures of between 60° and 150° C., preferably between 80° and 130° C., suitably under elevated pressures. The pressure is dependent on the particular nitrile employed and generally ranges between 50 and 500 atmospheres, preferably between 200 and 350 atmospheres.

The hydrogenation advantageously is conducted in the presence of ammonia. A particular advantage of the above-described catalysts is that a relatively small addition of ammonia is sufficient to extensively suppress the formation of secondary amines in the case of mono-nitriles, and/or imines and polyimines in the case of dinitriles. An addition of more than 10 mols of ammonia per mol of nitrile is recommended with conventional catalysts. When employing the catalysts of this invention, about 1 – 5 mols, preferably 2 – 4 mols, of ammonia per mol of nitrile is sufficient.

Inert diluents, e.g. methanol, cyclohexane and similar hydrogenation solvents can be employed. However, when employing such diluents, these is the danger that part of the alkali will be washed off from the surface of the support material. Therefore, when employing a hydrogenation solvent, it is advantageous to add a hydroxide or carbonate of an alkali metal to the hydrogenation mixture in an amount of about 0.1 – 5%, preferably 0.2 – 2%, based on the hydrogenation mixture. This ensures that the alkali concentration as provided for by this invention remains on the surface of the hydrogenation catalyst. The process can be conducted batchwise as well as continuously.

The lifetime of the catalysts is determined, not so much by a reduction of the catalytic activity but rather in a build-up of a pressure differential between the inlet and the outlet of the reactor as a result of deposits on the catalyst surface or the decomposition of the catalyst. Generally, hydrogenation must be terminated when this pressure difference exceeds 50 atmospheres. When employing the catalysts of this invention, hydrogenation can be conducted for a substantially longer period of time before this pressure differential is reached, e.g. on the order of months as compared to weeks when using the prior art catalysts.

The catalysts employed in accordance with this invention provide a long operating time with excellent yields and conversions, especially when using an inert hydrogenation diluent, e.g. methanol. A further advantage of the present catalysts is that they are economical. However, these advantages are attainable only if a support material as defined herein is employed.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLES

Employing the supports set forth in Table 1, the catalysts listed in Table 2 are produced in accordance with conventional methods. 1100 g of a support material according to the invention is impregnated by sprinkling with a solution of salts of cobalt, manganese and silver onto the support material. This procedure is carried out by heating in a rotating drum. The sprinkling takes place so slowly that the water is vaporized at once and the surface of the material is therefore kept dry. 2380 g of a solution containing 12.2 % Co, 3.22 % Mn and 0.19 % Ag are used; after this step the catalyst is heated in a air-stream for 16 hours at 350° C.

To conduct the hydrogenation process of this invention, 1.3 liter of the selected catalyst is filled into a tubular pressurized oven provided with electric heating. The catalyst is reduced at 150° – 350° C. under a total pressure of 120 atmospheres gauge, with a rising concentration of hydrogen in nitrogen. Under a hydrogen pressure of 300 atm. gauge, 140 ml./h. of dodecanedioic acid dinitrile, mixed with 60 ml./h. of methanol and 50 ml./h. of liquid ammonia, is passed over the catalyst at a temperature of 80° – 130° C.

In addition to the conversion, the pressure difference between the reactor inlet and outlet was determined. The results of the hydrogenations are set forth in Table 3. Experiments A – C are comparative experiments employing conventional catalysts, catalyst C being identical with the prior art catalyst described in Example 1 of Hoeckele U.S. Pat. No. 3,588,709. Whereas both types of catalysts achieve conversion rates of 98% after 12 days of hydrogenation, catalyst C imparted a pressure difference in excess of 50 atmospheres, the catalyst was entirely disintegrated and the reactor was clogged. In marked contrast thereto, the corresponding catalysts of this invention (Catalysts 1, 2, 3 and 4) had catalyst lives of 55 days or more, a more than 4 fold greater effective catalyst life. There was either no or substantially less than 50 atmosphere increase in pressure differential because the physical structure of the catalysts of the above-identified application were virtually unchanged with no or minor deposits on its surface. The above differences in effective catalyst life are of substantial economic significance when conducting continuous hydrogenations on a commercial scale.

TABLE 1

| Support | A Pumice | B (b) | C α-$Al_2O_3$ | 1 (b) | 2 (A) (B) | 3 $Al_2O_3$ | 4 $Al_2O_3$ (a) |
|---|---|---|---|---|---|---|---|
| Spec. Surface ($m^2$/g.) | ~1 | 0.5 | 8 | 0.5 | 0.5 | 0.1 | 0.5 |
| Pore Volume (ml./g.) | 0.7 | 0.35 | 0.55 | 0.35 | 0.35 | 0.38 | 0.25 |
| Annealing Loss (%) | 4.7 | 0.04 | 0.05 | 0.04 | 0.04 | 0.01 | 0.03 |
| Piled Weight (g./l.) | 450 | 700 | ~850 | 700 | 700 | 850 | 980 |
| Free Alkali Content (in % Oxide) | ~0.2 | 0 | 0 | 0.2 | 4 | 0.11 | 15.1 |
| CaO (%) | ~1 | 1 | — | 2 | 2 | 0.02 | 0.02 |
| $Fe_2O_3$ (%) | ~1 | 0.4 | 0 | 0.4 | 0.4 | 0.2 | 0.17 |
| $Al_2O_3$ (%) | ~15 | — | 99 | — | — | 84.7 | 72 |
| $SiO_2$ (%) | ~74 | 96.5 | — | 92 | 88 | 13.4 | 11.4 |
| Total Alkali Content (in % Oxide) | ~9 | 5.0 | 0.06 | 5.2 | 9.1 | 1.3 | 16.2 |

(a) The free alkali content was increased by spraying of soda solution.
(b) Silica containing small amounts of oxides of Na, Fe, Ca, and Mg.

TABLE 2

| Catalyst | A Pumice | B | C α-$Al_2O_3$ | 1 | 2 | 3 $Al_2O_3$ | 4 $Al_2O_3$ |
|---|---|---|---|---|---|---|---|
| Spec. Surface ($m^2$/g.) | 5 | 5 | 27 | 2 | 3 | 1.2 | 3 |
| Pore Volume (ml./g.) | 0.5 | 0.17 | 0.35 | 0.15 | 0.16 | 0.22 | 0.13 |
| Annealing Loss (%) | 1.8 | 2.8 | 2.0 | 2.2 | 2.0 | 1.3 | 2.3 |
| Piled Weight (g./l.) | 800 | 1300 | 1070 | 1390 | 1320 | 1250 | 1310 |
| Free Alkali Content (in % Oxide) | 0.12 | 0 | 0.00 | 0.1 | 2.3 | 0.03 | 10.8 |
| CaO (%) | 0.58 | 0.58 | 0 | 1.2 | 1.2 | 0.014 | 0.01 |
| $Fe_2O_3$ (%) | 0.58 | 0.23 | 0 | 0.23 | 0.25 | 0.14 | 0.12 |
| $Al_2O_3$ (%) | 8.7 | — | 72.5 | — | — | 61 | 57 |
| $SiO_2$ (%) | 43.0 | 56 | 0 | 54 | 51 | 9.6 | 8.2 |
| Total Alkali Content (in % Oxide) | 5.2 | 2.9 | 0.04 | 3.0 | 5.3 | 0.9 | 11.6 |
| Cobalt (in % Metal) | 24.0 | 24.0 | 15.4 | 24.0 | 22.2 | 16.3 | 16.1 |
| Manganese (in % Metal) | 6.6 | 6.5 | 4.1 | 6.6 | 5.95 | 4.6 | 4.5 |
| Silver (in % Metal) | 0.4 | 0.38 | 0.23 | 0.4 | 0.34 | 0.26 | 0.25 |

TABLE 3

| Experiment | 1 | 2 | A | B | 3 | 4 | C |
|---|---|---|---|---|---|---|---|
| Conversion (%) | >98 | >98 | >98 | >98 | >98 | >98 | >98 |
| Operating Period (Days) | 55 | 60** | 12 | 40 | 60** | 60** | 12 |
| Pressure Difference (atm.)* | <50 | 0 | >50 | >50 | 10 | 0 | >50 |
| Remarks: | Catalyst is hardly disintegrated. Deposits on the surface. | No change in catalyst and its surface | Catalyst is entirely disintegrated. Reactor is clogged. | Catalyst is hardly disintegrated. Very large deposits on the surface. | Catalyst is hardly disintegrated. Minor deposits on the surface. | No Change in catalyst and its surface. | Catalyst is entirely disintegrated. Reactor is clogged. |

*Measured after the indicated operating time.
**Experiment was terminated; the catalyst was not consumed.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the catalytic hydrogenation of dodecanedioic acid dinitrile to the corresponding primary amine, which comprises:

hydrogenating dodecanedioic acid dinitrile with a hydrogenation catalyst comprising 5 – 35% by weight of at least one of catalytically active cobalt and nickel as the active component supported on one or more of aluminum oxide, silicic acid or silica containing small amounts of the oxides of Na, Fe, Ca and Mg wherein the specific surface area of the support material is 0.1 – 0.8 $m^2$/g., the pore volume thereof is 0.2 – 0.4 ml./g., the annealing loss is less than 0.1% and the extractable alkalinity of the support is 0.1 – 10% by weight of the support, said hydrogenation being conducted in the presence of a diluent and a sufficient amount of alkali to ensure that said alkali concentration remains on the surface of the hydrogenation catalyst.

2. A process according to claim 1, wherein the hydrogenation is conducted in the presence of a diluent and about 0.1 – 5% by weight, based on the hydrogenation mixture, of a hydroxide or carbonate of an alkali metal.

3. A process according to claim 2, wherein said hydroxide or carbonate is present in an amount of about 0.2 – 2%, based on the hydrogenation mixture.

4. A process according to claim 1, wherein the hydrogenation is conducted in the presence of about 1 – 5 moles of ammonia per mole of nitrile.

5. A process according to claim 4, wherein 2 – 4 moles of ammonia per mole of nitrile are employed.

6. A process according to claim 1, wherein the support material is an oxide of aluminum.

* * * * *